(12) United States Patent
Hüffer et al.

(10) Patent No.: US 8,211,550 B2
(45) Date of Patent: Jul. 3, 2012

(54) COMPOUNDS AND THEIR USE FOR PRODUCING LEATHER AND AS DISPERSANTS

(75) Inventors: Stephan Hüffer, Ludwigshafen (DE); Sebastien Garnier, Weinheim (DE); Oliver Reese, Lemförde (DE); Günter Scherr, Ludwigshafen (DE); Harald Kiesow, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 366 days.

(21) Appl. No.: 12/377,360

(22) PCT Filed: Aug. 8, 2007

(86) PCT No.: PCT/EP2007/058209
§ 371 (c)(1),
(2), (4) Date: Feb. 12, 2009

(87) PCT Pub. No.: WO2008/022918
PCT Pub. Date: Feb. 28, 2008

(65) Prior Publication Data
US 2010/0227186 A1   Sep. 9, 2010

(30) Foreign Application Priority Data

Aug. 23, 2006 (EP) .................................. 06119375
Oct. 17, 2006 (EP) .................................. 06122437

(51) Int. Cl.
*C14C 9/00* (2006.01)
*C14C 13/02* (2006.01)

(52) U.S. Cl. ....... 428/540; 252/8.57; 544/196; 544/198; 8/147; 8/150; 8/150.5; 524/843

(58) Field of Classification Search ................. 524/101, 524/843; 428/540; 544/196, 198; 8/147, 8/150, 150.5
See application file for complete search history.

(56) References Cited

U.S. PATENT DOCUMENTS

| | | | |
|---|---|---|---|
| 3,533,977 A | 10/1970 | Read | |
| 3,812,122 A | 5/1974 | Lengsfeld | |
| 5,186,846 A | 2/1993 | Brueckmann et al. | |
| 2006/0063844 A1* | 3/2006 | Nagy et al. ...................... | 516/59 |
| 2008/0201864 A1* | 8/2008 | Wolf et al. ...................... | 8/94.22 |

FOREIGN PATENT DOCUMENTS

| | | |
|---|---|---|
| DE | 21 18 868 | 10/1972 |
| DE | 101 43 984 | 4/2002 |
| EP | 0459168 A2 | 12/1991 |
| GB | 599 261 | 3/1948 |
| WO | WO-2004072307 A1 | 8/2004 |
| WO | WO-2005040490 A1 | 5/2005 |

OTHER PUBLICATIONS

Database WPI Week 199331 Derwent Publications Ltd., London, GB; AN 1993-247938 XP002459201 & RO 103351A, abstract.
Ullmann's Encyclopedia of Industrial Chemistry, vol. A15, pp. 259 to 282, 5th edition (1990), Verlag Chemie Weinheim.
English Translation—Submission of International Preliminary Report on Patentability (IPRP), May 14, 2009.

* cited by examiner

*Primary Examiner* — James J Seidleck
*Assistant Examiner* — Deve E Valdez
(74) *Attorney, Agent, or Firm* — Connolly Bove Lodge & Hutz LLP

(57) ABSTRACT

A process for the production of leather using one or more reaction products of
(a) triamines or higher amines with
(b) at least one compound of the general formula I $$A^1\text{-}R^1 \qquad\qquad I$$

where $R^1$ is selected from hydrocarbon radicals having 10 to 5000 carbon atoms, straight-chain or branched, saturated or having from one to three C—C double bonds, and $A^1$ from groups capable of reacting with amines.

8 Claims, No Drawings

COMPOUNDS AND THEIR USE FOR PRODUCING LEATHER AND AS DISPERSANTS

CROSS REFERENCE TO RELATED APPLICATIONS

This application is a National Stage of PCT/EP2007/058209 filed Aug. 8, 2007 which in turn claims priority from European Application 06119375.1 filed Aug. 23, 2006 and European Application 06122437.4 filed Oct. 17, 2006, the entire contents of which are incorporated herein by reference.

The present invention relates to a process for the production of leather using one or more reaction products of
(a) at least one triamine or higher amine
(b) with at least one compound of the general formula I $$A^1\text{-}R^1 \qquad\qquad I$$

where $R^1$ is selected from hydrocarbon radicals having 10 to 5000 carbon atoms, straight-chain or branched, saturated or having from one to three C—C double bonds, and $A^1$ from groups capable of reacting with amines. The present invention furthermore relates to compounds with the use of which the abovementioned process can be particularly readily carried out. The present invention furthermore relates to leathers which are produced by the process according to the invention, and the use thereof.

Leathers are used in the production of numerous articles, for example of interior automotive parts, pieces of furniture and clothing, such as jackets, shoes and coats. High-quality articles of clothing are of particular interest there. For cleaning and care, for example after severe soiling, it is desirable to wash such articles of clothing. However, it is observed that such articles of clothing show a sharp decline in quality after a few washes and in some cases even after a single wash. During washing, as a rule the softening fatliquoring components are at least partly extracted, which manifests itself, inter alia, in embrittlement of the leather, in a loss of depth of color, in particular in graying of black leather, and generally in an unpleasant handle. Thus, the color declines and the handle becomes unpleasant. In specific cases, even cracking is found.

Numerous attempts have been made to solve the problem by carrying out chemical, for example covalent, fixing of the dyes, cf. for example WO 05/40490. Nevertheless, it is observed that the dyeing, for example of riding breeches produced from leather, declines in brilliance after a few washes and the handle is less pleasant.

It was therefore the object to provide a process for the production of leather which avoids the abovementioned disadvantages and gives leather having good stability of the dyeing and further good performance characteristics, in particular good handle.

Accordingly, the process defined at the outset was found.

The process defined at the outset is carried out starting from hides pretreated by conventional methods and originating from animals such as, for example, cattle, pigs, goats or deer, the so-called pelts. For the process according to the invention, it is not important whether, for example, the animals were killed by slaughtering or died of natural causes. The conventional methods of pretreatment include, for example, liming, deliming, bating and pickling and mechanical operations, for example the fleshing of the hides.

The process according to the invention is carried out using one or more reaction products obtainable by reacting
(a) at least one triamine or higher amine with
(b) at least one compound of the general formula I $$A^1\text{-}R^1 \qquad\qquad I$$

where $R^1$ is selected from hydrocarbon radicals having 10 to 5000 carbon atoms, straight-chain or branched, saturated or having from one to three C—C double bonds, and $A^1$ from groups capable of reacting with amines. Such reaction products of triamine (a) or higher amine (a) with compound of the general formula I (b) are also referred to below as reaction products used according to the invention.

Triamines (a) in the context of the present invention have three identical or different amino groups per molecule, selected from primary and secondary amino groups. Higher amines in the context of the present invention have at least four amino groups per molecule selected from primary and secondary amino groups. Tertiary amino groups are not taken into account.

Suitable triamines (a) are, for example, aliphatic triamines, such as diethylenetriamine and in particular trigonal planar triamines, "trigonal planar" relating to the arrangement of the amino groups. Examples of trigonal planar triamines are aromatic triamines, such as, for example, 1,3,5-triaminobenzene and very particularly preferably melamine.

In an embodiment of the present invention, higher amines are selected from condensates of melamine with at least one carbonyl compound selected from formaldehyde, acetaldehyde and urea.

In another embodiment of the present invention, higher amines are selected from condensates of melamine with formaldehyde and urea.

In a further embodiment of the present invention, higher amines (a) are selected from condensates of melamine with formaldehyde, urea and an aromatic amine, such as, for example, aniline, so-called aniline resin oils. Suitable aniline resin oils may have, for example, an amine number in the range of from 1 to 300 mg KOH/g, determined according to DIN 53176. Suitable aniline resin oils may have a molecular weight $M_n$ in the range of from 100 to 10 000 g/mol, determined according to DIN 55672-1.

Triamine (a) or higher amine (a) is reacted with (b) at least one compound of the general formula I $$A^1\text{-}R^1 \qquad\qquad I$$

Here, the variables are defined as follows:

$A^1$ is a group capable of reacting with amine, i.e. a group which can undergo an addition reaction or preferably substitution reaction with an organic amino group. Examples of groups which can undergo an addition reaction with amine are isocyanate groups and examples of groups capable of Michael addition reactions are, for example, —CO—CH═$CH_2$ groups.

Preferred as $A^1$ are those groups which can undergo a substitution reaction with amino groups, in particular carbonyl groups and carboxyl groups. Examples are acid chloride groups (CO—Cl), chloroformic ester groups (O—CO—Cl), $C_1$-$C_4$-alkyl ester groups, in particular ethyl and methyl ester groups, and carboxylic anhydride groups, in particular succinic anhydride groups.

$R^1$ is selected from hydrocarbon radicals having from 10 to 5000 carbon atoms, preferably 15 to 2500 carbon atoms, particularly preferably up to 500 carbon atoms, linear or preferably branched, saturated or having up to 3 C—C double bonds, which may have a cis or trans configuration or be present as a methylidene group. $R^1$ preferably has no heteroatoms.

Preferred examples of $R^1$ are n-alkyl radicals having 10 to 40 carbon atoms, preferably 12 to 20 carbon atoms, for example n-$C_{12}H_{25}$, n-$C_{14}H_{29}$, n-$C_{16}H_{33}$, n-$C_{18}H_{37}$ and n-$C_{20}H_{41}$.

Particularly preferred examples of $R^1$ are polyisobutenyl radicals, in particular those of the formula

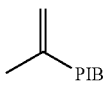

where PIB is a radical which is derived from polyisobutene, for example $(CH_3)_3C—[CH_2—C(CH_3)_2]_n—CH_2—$ where n may be a number in the range of from 1 to about 5000, preferably from 2 to about 2500, particularly preferably up to 500. n is as a rule an average value (number average), and n may be a non-integral number.

In an embodiment of the present invention, up to 20 mol %, preferably from 1 to 10 mol %, of the $[CH_2—C(CH_3)_2]$ units in the PIB are replaced by one or more straight-chain or preferably branched $C_4$-$C_{10}$-olefins. The following may be mentioned by way of example: 1-pentene, 2-methylbut-1-ene, 1-hexene, 2-methylpent-1-ene, 2-methylhex-1-ene, 2,4-dimethyl-1-hexene, diisobutene (mixture of 2,4,4-trimethyl-1-pentene and 2,4,4-trimethyl-2-pentene), 2-ethylpent-1-ene, 2-ethylhex-1-ene and 2-propylhept-1-ene, 1-octene, 1-decene and 1-dodecene and styrene.

In another embodiment of the present invention, PIB is a radical which, apart from isobutene, comprises no further olefins incorporated in the form of polymerized units.

Many compounds of the general formula I are known, and the preparation of some examples and the preparation of their homologs will be discussed in more detail below.

In an embodiment of the present invention the process according to the invention is carried out as a tanning process, also referred to below as tanning process according to the invention, preferably as a retanning process, also referred to below as retanning process according to the invention.

The tanning process according to the invention is carried out in general in such a way that one or more reaction products used according to the invention are added in one portion or in a plurality of portions immediately before or during the tanning step. The tanning process according to the invention is preferably carried out at a pH of from 2.5 to 4, it frequently being observed that the pH increases by about 0.3 to three units while the tanning process according to the invention is being carried out.

The tanning process according to the invention is carried out in general at temperatures of from 10 to 45° C., preferably at from 20 to 30° C. A duration of from 10 minutes to 12 hours has proven useful, and from one to three hours are preferred. The tanning process according to the invention can be carried out in any desired vessels customary in the tannery, for example by drumming in barrels or in rotating drums.

In an embodiment of the present invention, altogether from 0.01 to 10% by weight of reaction product used according to the invention, based on the shaved weight, preferably from 0.5 to 3% by weight, are used.

In a variant of the tanning process according to the invention, reaction product used according to the invention is used together with one or more conventional tanning agents, for example with chrome tanning agents, mineral tanning agents, syntans, polymer tanning agents or vegetable tanning agents, as described, for example, in *Ullmann's Encyclopedia of Industrial Chemistry*, volume A15, pages 259 to 282 and in particular page 268 et seq., 5th edition (1990), Verlag Chemie Weinheim. The weight ratio of product obtained by reacting triamine (a) or higher amine (a) with compound of the general formula I (b): conventional tanning agent or sum of the conventional tanning agents is expediently from 0.01:1 to 100:1. In an advantageous variant of the process according to the invention, only a few ppm of conventional tanning agents are added to the above-described product obtained by reacting triamine (a) or higher amine (a) with compound of the general formula I (b).

In a variant of the tanning process according to the invention, reaction product used according to the invention is used together with one or more fatliquoring agents or oleophilic components.

In a variant of the tanning process according to the invention, reaction product used according to the invention is added in one portion or in a plurality of portions before or during the pretanning. Addition in the pickle is also conceivable.

The retanning process according to the invention is carried out starting from semi-finished products tanned conventionally, i.e. for example with chrome tanning agents, mineral tanning agents, polymer tanning agents, aldehydes, syntans or resin tanning agents, or semi-finished products produced according to the invention as described above. For carrying out the retanning according to the invention, at least one reaction product used according to the invention is allowed to react on semi-finished products, i.e. treatment with at least one reaction product used according to the invention is effected.

The retanning process according to the invention can be carried out under otherwise conventional conditions. Expediently, one or more, i.e. from 2 to 6, soaking steps are chosen and washing with water can be effected between the soaking steps. The temperature during the individual soaking steps is in each are from 5 to 60° C., preferably from 20 to 45° C. Expediently, one or more further compositions usually used during the retanning are employed, for example fatliquors, polymer tanning agents and acrylate- and/or methacrylate-based fatliquoring agents, retanning agents based on vegetable tanning agents, fillers, leather dyes or emulsifiers.

In an embodiment of the present invention, treatment with at least one hydrophobic compound, preferably selected from silicones, natural fats and preferably polyisobutene, is additionally effected. Polyisobutene is understood as meaning homopolymers and copolymers of isobutene with up to 20 mol % of propylene, 1-pentene, 2-methylbut-1-ene, 1-hexene, 2-methylpent-1-ene, 2-methylhex-1-ene, 2,4-dimethylhex-1-ene, diisobutene (mixture of 2,4,4-trimethyl-1-pentene and 2,4,4-trimethyl-2-pentene), 2-ethylpent-1-ene, 2-ethylhex-1-ene and 2-propylhept-1-ene, 1-octene, 1-decene and 1-dodecene or vinylaromatics, such as styrene and α-methylstyrene, $C_1$-$C_4$-alkylstyrene such as, for example, 2-, 3- and 4-methylstyrene and 4-tert-butylstyrene, very particularly preferably homopolymers of isobutene. In the context of the present invention, polyisobutene may have, per molecule, one ethylenically unsaturated group which may be present in the form of a vinyl, vinylidene or alkylvinylidene group.

In an embodiment of the present invention, polyisobutene has an average molecular weight $M_n$ of up to 50 000 g/mol, preferably from 300 to 25 000 g/mol, particularly preferably from 400 to 10 000 g/mol, very particularly preferably from 500 to 5000 g/mol and even more preferably up to 1200 g/mol, determined, for example, by gel permeation chromatography (GPC).

In an embodiment of the present invention, polyisobutene has a polydispersity $M_w/M_n$ in the range of from 1.1 to 10, preferably up to 3 and particularly preferably from 1.5 to 2.0.

In an embodiment, polyisobutene has a monomodal molecular weight distribution. In another embodiment of the present invention, polyisobutene has a polymodal and in particular a bimodal molecular weight distribution with a maximum of $M_n$ in the range of from 500 to 1200 g/mol and a local maximum of $M_n$ in the range of from 2000 to 50 000 g/mol, particularly preferably up to 10 000 g/mol.

The present invention furthermore relates to leathers produced by the process according to the invention. Leathers according to the invention are distinguished by good fullness, softness and intensity and stability of the dyeing to washing and further good performance characteristics. Leathers according to the invention are suitable, for example, for the production of shoes or interior automotive parts, such as, for example, car seats, and in particular for the production of articles of clothing, such as, for example, belts, jackets, coats and pants, in particular sports pants, such as, for example, riding breeches and furthermore, for example, for the production of pieces of furniture and of handbags.

The present invention furthermore relates to compounds of the formula II

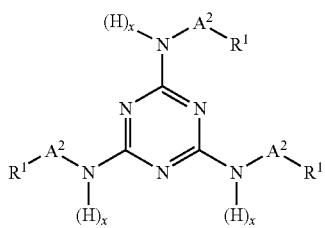

in which the variables are defined as follows:
$R^1$ are identical or different and are selected from hydrocarbon radicals having 10 to 5000 carbon atoms, straight-chain or branched, saturated or having up to three C—C double bonds,
$N$-$A^2$ are identical or different and are selected from functional units which form by reaction of groups $A^1$ capable of reacting with amine in the reaction with amine,
x are identical or different and in each case are selected from zero or one, preferably in each case are zero.

$R^1$ is selected from hydrocarbon radicals having 10 to 5000 carbon atoms, preferably 15 to 2500 carbon atoms, particularly preferably up to 500 carbon atoms, linear or preferably branched, saturated or having up to 3 C—C double bonds, which may have a cis or trans configuration or may be present as a methylidene group. $R^1$ preferably has no heteroatoms.

Preferred examples of $R^1$ are n-alkyl radicals having 10 to 40 carbon atoms, preferably 12 to 20 carbon atoms, for example n-$C_{12}H_{25}$, n-$C_{14}H_{29}$, n-$C_{16}H_{33}$, n-$C_{18}H_{37}$ and n-$C_{20}H_{41}$.

Particularly preferred examples of $R^1$ are polyisobutenyl radicals, in particular those of the formula

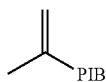

where PIB is a radical which is derived from polyisobutene, for example

where n may be a number in the range of from 1 to about 5000, preferably from 2 to about 2500, particularly preferably up to 500. n is as a rule an average value (number average), and n may also be a non-integral number.

In an embodiment of the present invention, up to 20 mol %, preferably from 1 to 10 mol %, of the $[CH_2$—$C(CH_3)_2]$ units in the PIB are replaced by one or more straight-chain or preferably branched $C_4$-$C_{10}$-olefins. The following may be mentioned by way of example: 1-pentene, 2-methylbut-1-ene, 1-hexene, 2-methylpent-1-ene, 2-methylhex-1-ene, 2,4-dimethyl-1-hexene, diisobutene (mixture of 2,4,4-trimethyl-1-pentene and 2,4,4-trimethyl-2-pentene), 2-ethylpent-1-ene, 2-ethylhex-1-ene and 2-propylhept-1-ene, 1-octene, 1-decene and 1-dodecene and styrene.

In another embodiment of the present invention, PIB is a radical which, apart from isobutene, comprises no further olefins incorporated in the form of polymerized units.

$N$-$A^2$ are in each case identical or different and are selected from functional units which form by reaction of amine with a group $A^1$ capable of reacting with amine in the reaction with amine. Thus, where $A^1$ is an isocyanate group, $N$-$A^2$ is an N—CO—NH group. Where $A^1$ is a chlorocarbonic ester group, $N$-$A^2$ is an N—CO—O group. In the abovementioned cases, x is preferably one in each case.

Where $A^1$ is selected from acid chloride groups (CO—Cl) and $C_1$-$C_4$-alkyl ester groups, in particular ethyl and methyl ester groups, $N$-$A^2$ is preferably an amido group and x is in each case one.

In an embodiment of the present invention, $A^1$ is a succinic anhydride group and $N$-$A^2$ is an imido group of the formula

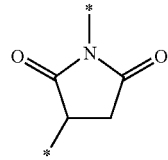

and x is in each case zero.

The present invention furthermore relates to compounds of the general formula III and preferably III b

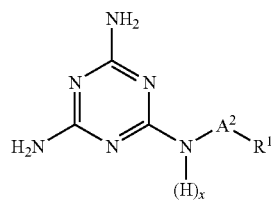

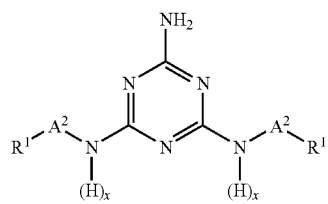

in which the variables are as defined above.

Compounds according to the invention of the formula III a, preferably III b and in particular II are particularly suitable for carrying out the process for the production of leather. The present invention furthermore relates to the use of a compound according to the invention for the production of leather, for example as a tanning agent or retanning agent.

The present invention furthermore relates to a process for the preparation of compounds according to the invention, also referred to below as preparation process according to the invention. The preparation process according to the invention can be carried out by a procedure in which triamine or higher amine, preferably melamine, is reacted with at least one compound of the general formula I.

Compounds of the general formula I and their preparation are known per se. Particularly preferred compounds of the general formula I in which $R^1$ is selected from hydrocarbon radicals of the formula

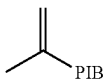

can be prepared by functionalizing so-called reactive polyisobutene, i.e. polyisobutene having at least one C—C double bond. Methods for functionalizing polyisobutene are known per se, and the following may be mentioned by way of example:
i) reaction of polyisobutene with an equimolar amount of peroxy compound, for example $H_2O_2$ or a peroxycarboxylic acid, such as meta-chloroperbenzoic acid, to give an epoxidized polyisobutene,
ii) reaction of polyisobutene with an alkene which has a double bond substituted by one or preferably more electron-attracting groups (enophile), in an ene reaction, a particularly preferred enophile being maleic anhydride,
iii) reaction of polyisobutene with carbon monoxide and hydrogen in the presence of a hydroformylation catalyst to give a hydroformylated polyisobutene,
iv) reaction of polyisobutene with a phosphorus halide or a phosphorus oxychloride to give a polyisobutene functionalized with phosphonyl groups.

In an embodiment of the present invention, melamine is reacted with a compound of the general formula IV

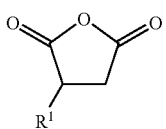

IV where $R^1$ is as defined above.

The preparation process according to the invention can be carried out at room temperature. However, it is preferable to carry out the preparation process according to the invention at elevated temperature, for example at from 50 to 200° C., preferably from 150 to 195° C.

The preparation process according to the invention can be carried out at atmospheric pressure. In an embodiment of the present invention, the preparation process according to the invention is carried out at elevated pressure, for example at from 1.1 to 10 bar. In another embodiment of the present invention, the process according to the invention is carried out at reduced pressure, for example at from 10 to 750 mbar.

In an embodiment of the present invention, triamine, in particular melamine, and compound of the formula I can be used in a stoichiometric ratio based on amino groups. In a preferred embodiment of the present invention, an excess of compound I is used, for example a 1.1- to 10-fold excess, based on amino groups.

In an embodiment of the present invention, higher amine and compound of the general formula I are used in a stoichiometric ratio, based on amino groups of higher amine. In a preferred embodiment of the present invention an excess of compound I is used.

In an embodiment of the present invention, the preparation process according to the invention can be carried out using a solvent. High-boiling solvents, such as, for example xylenes or ethylbenzene, and furthermore N,N-dimethylformamide are particularly suitable. In a preferred embodiment of the present invention, the preparation process according to the invention is carried out without using solvents.

In an embodiment of the present invention, after the reaction is complete, the compound according to the invention can be purified, for example by extraction. In a preferred embodiment of the present invention, however, purification steps are omitted and the crude product obtained is used for the process according to the invention.

In an embodiment of the present invention, the compound according to the invention is contaminated with compound of the general formula I when used for the production of leather.

In an embodiment of the present invention, the compound according to the invention is contaminated with hydrolyzed compound of the general formula I when used for the production of leather. Thus, for example when the compound of the general formula I is PIBSA

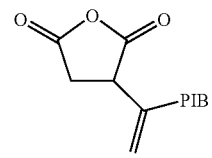

a compound of the formula

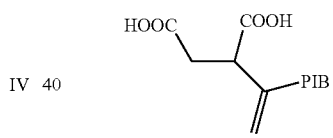

can be detected as an impurity when used for the production of leather.

In particular, polyisobutene, reactive (having a C—C double bond) or unreactive (no C—C double bonds or one internal C—C double bond per molecule), can be found as an impurity in many cases.

In particular, the corresponding compounds of the formula III a and preferably III b can be found as an impurity in compounds of the formula II.

Conversely, the corresponding compounds of the general formulae III a and II can be found as an impurity in compounds according to the invention of the general formula III b.

In an embodiment of the present invention, compounds according to the invention of the formula III a, preferably III b and in particular II have a dynamic viscosity in the range of from 500 to 500 000, preferably from 2500 to 250 000, mPa·s, determined at 23° C., for example according to ISO standard 3219.

A further aspect of the present invention relates to mixtures comprising at least one compound according to the invention of the formula III a, preferably III b and in particular II, as described above, and polyisobutene. The process according to the invention for the production of leather can also be very readily carried out using mixtures according to the invention.

The present invention therefore furthermore relates to the use of mixtures according to the invention as assistants for leather production. A further aspect of the present invention is a process for the production of leather using at least one mixture according to the invention. The last-mentioned process according to the invention can be carried out in particular as a tanning or retanning process. The applicable process conditions are in principle the abovementioned ones.

In an embodiment of the present invention, compound according to the invention of the formula III a, preferably III b and in particular II and polyisobutene are present in a weight ratio in the range of from 20:1 to 5:1, preferably from 12:1 to 8:1.

In an embodiment of the present invention, mixtures according to the invention have a dynamic viscosity in the range of from 10 000 to 500 000, preferably from 50 000 to 250 000 mPa·s, determined at 23° C., for example according to ISO standard 3219.

A further aspect of the present invention is the use of compounds according to the invention of the formula III a, preferably III b and in particular II, in pure form or in the form of a mixture according to the invention, as dispersants (compatibilizers) for hydrophobic compounds, such as, for example, silicones, in particular polydimethylsilicone, for polyolefin waxes having a molecular weight $M_w$ in the range of from 1000 to, for example, 20 000 g/mol, such as, for example, polypropylene waxes or polyethylene waxes, in unoxidized or in partly oxidized form, for polyisobutene or for natural fats. With the aid of a compound according to the invention, above-mentioned hydrophobic substances can be dispersed in aqueous and non-aqueous solvents and/or the establishment of the partition equilibrium in mixtures of water and water-immiscible solvents can be accelerated. As a rule, stable dispersions are obtained, which can be applied, for example, to surfaces to be rendered water repellent, in particular to animal hides or leather, and very stable water repellency and/or fatliquoring can be achieved.

A further aspect of the present invention is the use of compounds according to the invention of the formula III a, preferably III b and in particular II, in pure form or in the form of a mixture according to the invention, as dispersants for pigments, inorganic or organic, and in particular for carbon black and iron oxide.

In the context of the present invention, pigments are to be understood as meaning virtually insoluble, dispersed, finely divided, organic or inorganic colorants according to the definition in DIN 55944.

Pigments Selected by Way of Example Are
monoazo pigments, such as, for example C.I. Pigment Brown 25, C.I. Pigment Orange 5, 13, 36 und 67, C.I. Pigment Red 1, 2, 3, 5, 8, 9, 12, 17, 22, 23, 31, 48:1, 48:2, 48:3, 48:4, 49, 49:1, 52:1, 52:2, 53, 53:1, 53:3, 57:1, 63, 112, 146, 170, 184, 210, 245 und 251, C.I. Pigment Yellow 1, 3, 73, 74, 65, 97, 151 and 183,
disazo pigments, such as, for example, C.I. Pigment Orange 16, 34 und 44, C.I. Pigment Red 144, 166, 214 und 242; C.I. Pigment Yellow 12, 13, 14, 16, 17, 81, 83, 106, 113, 126, 127, 155, 174, 176 and 188,
anthanthrone pigments, such as, for example, C.I. Pigment Red 168 (C.I. Vat Orange 3),
anthraquinone pigments, such as, for example, C.I. Pigment Yellow 147 and 177, C.I. Pigment Violet 31,
anthraquinone pigments, such as, for example, C.I. Pigment Yellow 147 and 177, C.I. Pigment Violet 31,
anthrapyrimidine pigments, such as, for example, C.I. Pigment Yellow 108 (C.I. Vat Yellow 20)
quinacridone pigments, such as, for example, C.I. Pigment Red 122, 202 and 206, C.I. Pigment Violet 19,
quinophthalone pigments, such as, for example, C.I. Pigment Yellow 138,
dioxazine pigments, such as, for example, C.I. Pigment Violet 23 and 37,
flavanthrone pigments, such as, for example, C.I. Pigment Yellow 24 (C.I. Vat Yellow 1),
indanthrone pigments, such as, for example, C.I. Pigment Blue 60 (C.I. Vat Blue 4) and 64 (C.I. Vat Blue 6),
isoindoline pigments, such as, for example, C.I. Pigment Orange 69, C.I. Pigment Red 260, C.I. Pigment Yellow 139 and 185,
isoindolinone pigments, such as, for example, C.I. Pigment Orange 61, C.I. Pigment Red 257 and 260, C.I. Pigment Yellow 109, 110, 173 and 185,
isoviolanthrone pigments, such as, for example, C.I. Pigment Violet 31 (C.I. Vat Violet 1),
metal complex pigments, such as, for example, C.I. Pigment Yellow 117, 150 and 153, C.I. Pigment Green 8,
perinone pigments, such as, for example, C.I. Pigment Orange 43 (C.I. Vat Orange 7), C.I. Pigment Red 194 (C.I. Vat Red 15),
perylene pigments, such as, for example, C.I. Pigment Black 31 and 32, C.I. Pigment Red 123, 149, 178, 179 (C.I. Vat Red 23), 190 (C.I. Vat Red 29) and 224, C.I. Pigment Violet 29,
phthalocyanine pigments, such as, for example, C.I. Pigment Blue 15, 15:1, 15:2, 15:3, 15:4, 15:6 and 16, C.I. Pigment Green 7 and 36,
pyranthrone pigments, such as, for example, C.I. Pigment Orange 51, C.I. Pigment Red 216 (C.I. Vat Orange 4),
thioindigo pigments, such as, for example, C.I. Pigment Red 88 and 181 (C.I. Vat Red 1), C.I. Pigment Violet 38 (C.I. Vat Violet 3),
triarylcarbonium pigments, such as, for example, C.I. Pigment Blue 1, 61 and 62, C.I. Pigment Green 1, C.I. Pigment Red 81, 81:1 and 169, C.I. Pigment Violet 1, 2, 3 and 27, C.I. Pigment Black 1 (aniline black),
C.I. Pigment Yellow 101 (aldazine yellow),
C.I. Pigment Brown 22.

Examples of Inorganic Pigments are:
white pigments, such as, for example, titanium dioxide (C.I. Pigment White 6), zinc white, leaded zinc oxide, zinc sulfide, lithopone; lead white,
black pigments, such as, for example, iron oxide black (C.I. Pigment Black 11), iron manganese black, spinel black (C.I. Pigment Black 27),
colored pigments, such as, for example, chromium oxide, viridian green, chrome green (C.I. Pigment Green 48), cobalt green (C.I. Pigment Green 50), ultramarine green, cobalt blue (C.I. Pigment Blue 28 and 36), ultramarine blue, iron blue (C.I. Pigment Blue 27), manganese blue, ultramarine violet, cobalt and manganese violet, iron oxide red (C.I. Pigment Red 101); cadmium sulfoselenide (C.I. Pigment Red 108), molybdenum red (C.I. Pigment Red 104); ultramarine red, iron oxide brown, mixed brown, spinel and corundum phases (C.I. Pigment Brown 24, 29 and 31), chrome orange;
iron oxide yellow (Cl. Pigment Yellow 42); nickel titanium yellow (C.I. Pigment Yellow 53; C.I. Pigment Yellow 157 and 164); chrome titanium yellow; cadmium sulfide and cadmium zinc sulfide (C.I. Pigment Yellow 37 and 35); chrome yellow (C.I. Pigment Yellow 34), zinc yellow, alkaline earth metal chromates; Naples yellow; bismuth vanadate (C.I. Pigment Yellow 184);

interference pigments, such as, for example, metal effect pigments based on coated metal lamellae, pearl luster pigments based on metal oxide-coated mica lamellae, liquid crystal pigments.

Monoazo pigments, (in particular laked BONS pigments, naphthol AS pigments), disazo pigments (in particular diary) yellow pigments, bisacetoacetanilide pigments, disazopyrazoline pigments), quinacridone pigments, quinophthalone pigments, perinone pigments, phthalocyanine pigments, triarylcarbonium pigments (alkali blue pigments, laked rhodamines, dye salts having complex anions), isoindoline pigments and carbon blacks may be mentioned as preferred pigments.

Examples of particularly preferred pigments are: C.I. Pigment Yellow 138, C.I. Pigment Red 122, C.I. Pigment Violet 19, C.I. Pigment Blue 15:3 and 15:4, C.I. Pigment Black 7, C.I. Pigment Orange 5, 38 and 43 and C.I. Pigment Green 7.

The present invention furthermore relates to pigment concentrates comprising at least one pigment selected from organic and inorganic pigments and in particular carbon black, a compound according to the invention of the formula III a, preferably III b and in particular II or a mixture according to the invention. Pigment concentrates according to the invention may comprise, for example, from 60 to 95% by weight of pigment, from 5 to 40% by weight of compound according to the invention of the formula III a, preferably III b and in particular II and optionally up to 20% by weight of one or more polyethers, for example polyethylene glycol.

For the preparation of pigment concentrates according to the invention, it is possible to use, for example, those apparatuses in which high shear forces are exerted. Examples are comminution apparatuses, such as, for example, mills and in particular ball mills, e.g. stirred ball mills, and furthermore kneaders and extruders. For example, those apparatuses in which high shear forces are exerted can also be used for the further processing of pigment concentrates according to the invention, kneaders and extruders being mentioned in particular.

Pigment concentrates according to the invention can advantageously be used for coloring high molecular weight organic and inorganic materials, in particular plastics from the group consisting of the polycondensates and thermoplastic polymers.

A further aspect of the present invention is the use of compounds according to the invention of the formula III a, preferably III b and in particular II as nucleating agents for polymers, in particular for crystalline and semi-crystalline plastics, such as, for example, polyolefins, preferably polyethylene and polypropylene, polyvinyl chloride (PVC), polyamide, polybutylene terephthalate (PBT) and polycarbonates. If it is desired to use compounds according to the invention as nucleating agents, it is best to adopt a procedure in which one or more compounds according to the invention are mixed with the relevant polymer, for example with the use of an extruder. If a compound according to the invention is used as a nucleating agent, mechanical properties, optical properties (transparency) and the technical processability (rheology, cycle times, etc.) can be particularly readily controlled. At the same time, a further aspect of the present invention is a process for processing polymers, in particular crystalline and semi-crystalline plastics, using one or more compounds according to the invention of the formula III a, preferably III b and in particular II. If it is desired to use a compound according to the invention as a nucleating agent, in many cases from 10 ppm to not more than 2% by weight, preferably from 100 ppm to 2500 ppm, based on the relevant polymer, are sufficient.

A further aspect of the present invention is the use of compounds according to the invention of the formula III a, preferably III b and in particular II as compatibilizers for polymer blends. At the same time, the present invention relates to a process for the preparation of polymer blends using one or more compounds according to the invention of the formula III a, preferably III b and in particular II. A compound according to the invention of the formula III a, preferably III b and in particular II serves as a rule as a compatibilizer of two polymers which are incompatible per se, for example polyamide and polypropylene.

A further aspect of the present invention is the use of compounds according to the invention of the formula III a, preferably III b and in particular II as compatibilizers during the mixing of a polymer with at least one component of the mixture. Components of the mixture are selected, for example, from inorganic oxides, hydroxides and carbonates, for example magnesium oxide (talc), silica, mica, magnesium hydroxide, calcium hydroxide, aluminosilicates, chalk and furthermore glass fibers, natural fibers, carbon fibers, carbon black and preferably oxidic pigments, in particular iron oxide and titanium dioxide. If it is desired to use a compound according to the invention of the formula III a, preferably III b and in particular II as a compatibilizer, in many cases from 10 ppm to not more than 2% by weight, preferably from 100 ppm to 2500 ppm, based on the relevant polymer, are sufficient.

In a particular embodiment of the present invention, a compound according to the invention of the formula III a, preferably III b and in particular II is used as a compatibilizer for the preparation of wood-plastic composites. Wood is therefore used as a component of the mixture. The present invention therefore relates to a process for the preparation of wood-plastic composites using one or more compounds according to the invention of the formula III a, preferably III b and in particular II. Wood, in particular in the form of fibers or flour, and one or more polymers, in particular polyethylene or polypropylene, are mixed, it being possible to vary the ratios within wide ranges, for example in the range of from 10 to 90% by weight of polymer, from 10 to 90% by weight of wood and in the range of from 0.5 to 5% by weight of compound according to the invention.

The present invention furthermore relates to aqueous formulations, for example aqueous solutions, comprising at least one compound according to the invention of the formula III a, preferably III b and in particular II. Aqueous formations according to the invention may be yellowish or brownish and may have a solids content in the range of from 1 to 90% by weight, preferably from 30 to 75% by weight. Aqueous formulations according to the invention are particularly suitable for carrying out the process according to the invention for the production of leather and can be readily metered. The present invention furthermore relates to the use of an aqueous formulation according to the invention for the production of leather, for example as a tanning agent or retanning agent.

The invention is explained by working examples.

Dynamic viscosities were always determined according to ISO standard 3219—former DIN standard 53018.

I. Preparation of Compounds According to the Invention and Mixtures According to the Invention I.1 Preparation of Mixture I.1 According to the Invention In a glass flask having a stirrer, 0.47 g (0.0037 mol) of melamine was added to 50.0 g (0.039 mol) of polyisobutenylsuccinic anhydride having a hydrolysis number of 87.5 mg KOH/g ($M_{reactive}$=1282 g/mol) and heated to 170° C. The resulting reaction mixture was stirred for 4 hours at 170° C. and then cooled to room temperature. 41.1 g of mixture I.1 according to the invention was obtained as a homogeneous, transparent, dark brown, thick and tacky condensate. The dynamic viscosity was 158 000 mPa·s at 23° C. Characteristic peaks in the IR spectrum: 1780 cm$^{-1}$ and 1865 cm$^{-1}$, 1780 cm$^{-1}$ and 1714 cm$^{-1}$.

I.2 Preparation of Mixture 1.2 According to the Invention 1.89 g (0.015 mol) of melamine were added to 50.0 g (0.039 mol) of polyisobutenylsuccinic anhydride analogously to example I.1 and heated to 170° C. The resulting reaction mixture was stirred for 7 hours at 170° C. and then cooled to room temperature. 39.0 g of mixture I.2 according to the invention were obtained as a dark brown, thick and tacky condensate. The dynamic viscosity was 184 000 mPa·s at 23° C. Characteristic peaks in the IR spectrum: 1780 cm$^{-1}$ and 1712 cm$^{-1}$. Secondary peaks: 1780 cm$^{-1}$ and 1865 cm$^{-1}$.

I.3 Preparation of Mixture I.3 According to the Invention 0.82 g (0.0065 mol) of melamine was added to 46.5 g (0.0347 mol) of polyisobutenylsuccinic anhydride having a hydrolysis number of 155.8 ($M_{reactive}$=720 g/mol) and heated to 170° C. The resulting reaction mixture was stirred for 4 hours at 170° C. and then cooled to room temperature. 40.7 g of mixture I.3 according to the invention were obtained as a homogeneous, transparent, dark brown, thick and tacky condensate. The dynamic viscosity was 16 290 mPa·s at 40° C. Characteristic peaks in the IR spectrum: 1780 cm$^{-1}$ and 1865 cm$^{-1}$, 1780 cm$^{-1}$ and 1714 cm$^{-1}$.

I.4 Preparation of Mixture I.4 According to the Invention 0.25 g (0.002 mol) of melamine was added to 50.0 g (0.02 mol) of polyisobutenylsuccinic anhydride having a hydrolysis number of 45.6 ($M_{reactive}$=2460 g/mol) and heated to 120° C. The resulting reaction mixture was stirred for 6 hours at 120° C. and then cooled to room temperature. 44.4 g of mixture I.4 according to the invention were obtained as a homogeneous, transparent, dark brown, thick and tacky condensate. The dynamic viscosity was 244 000 mPa·s at 40° C. Characteristic peaks in the IR spectrum: 1780 cm$^{-1}$ and 1865 cm$^{-1}$, 1780 cm$^{-1}$ and 1713 cm$^{-1}$.

I.5 Preparation of Mixture I.5 According to the Invention 0.47 g (0.0037 mol) of melamine was added to 50.0 g (0.039 mol) of polyisobutenylsuccinic anhydride having a hydrolysis number of 87.5 mg KOH/g ($M_{reactive}$=1282 g/mol) and heated to 120° C. The resulting reaction mixture was stirred for 4 hours at 120° C. and then cooled to room temperature. 41.1 g of mixture I.5 according to the invention were obtained as a homogeneous, transparent, light brown, thick and tacky condensate. The dynamic viscosity was 32 590 mPa·s at 40° C. Characteristic peaks in the IR spectrum: 1780 cm$^{-1}$ and 1865 cm$^{-1}$, 1780 cm$^{-1}$ and 1714 cm$^{-1}$.

I.6 Preparation of Mixture I.6 According to the Invention

In a first stage, aniline resin oil as an example of a higher amine was prepared from melamine, aniline, urea and formaldehyde:

216.52 g (2.08 mol) of sodium hydrogen sulfite were initially taken in a three-necked flask. 59.13 g (1.97 mol) of formaldehyde were then added dropwise. The resulting mixture was heated to 90° C. and stirred for 10 minutes at 90° C. Thereafter, 37.30 g (0.40 mol) of aniline were added and the mixture was stirred for a further 15 minutes at 90° C. 15.00 g (0.12 mol) of melamine and 25.30 g (0.42 mol) of urea were added and 16.23 g (0.54 mol) of formaldehyde were slowly added dropwise. The resulting mixture was stirred for 4 hours at 90° C. and the resulting aniline resin oil was then cooled to room temperature. It had an amine number of 77.5 mg KOH/g, determined according to DIN 53176.

8.6 g (0.0039 mol, based on aniline) of aniline resin oil were added to 50.0 g (0.039 mol) of polyisobutenylsuccinic anhydride having a hydrolysis number of 87.5 ($M_{reactive}$=1282 g/mol) and heated to 130° C. The resulting reaction mixture was stirred for 7 hours at 130° C. and then cooled to room temperature. 47.7 g of a mixture according to the invention were obtained as a clear, light brown condensate having a homogeneous appearance and a viscosity of 277 000 mPa·s at 23° C.

I.7 Preparation of Mixture 1.7 According to the Invention

In a stirred apparatus, 19.73 g (0.156 mol) of melamine were added to 125.0 g (0.469 mol) of (Z)-dodecenylsuccinic anhydride (IV.2)

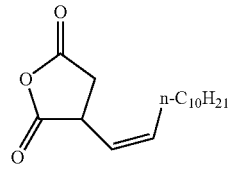

IV.2 and heated to 130° C. The resulting reaction mixture was stirred for 7 hours at 130° C. and then cooled to room temperature. 137.6 g of mixture I.7 according to the invention were obtained as a homogeneous, opaque, light brown, thick condensate. The dynamic viscosity was 750 mPa·s at 40° C. Characteristic peaks in the IR spectrum: 1785 cm$^{-1}$ and 1862 cm$^{-1}$, 1785 cm$^{-1}$ and 1712 cm$^{-1}$.

I.8 Preparation of Mixture I.8 According to the Invention 16.4 g (0.130 mol) of melamine were added to 500.0 g (0.392 mol) of polyisobutenyl-succinic anhydride having a hydrolysis number of 87.5 mg KOH/g ($M_{reactive}$=1282 g/mol) and heated to 300° C. The resulting reaction mixture was stirred for 4 hours at 300° C. and then cooled to room temperature. 434.5 g of mixture 1.8 according to the invention were obtained as a homogeneous, dark brown, thick and tacky condensate. The dynamic viscosity was 31 800 mPa·s at 40° C.

Characteristic peaks in the IR spectrum: 1780 cm$^{-1}$ and 1716 cm$^{-1}$.

I.9 Preparation of Mixture I.9 According to the Invention 4.1 g (0.033 mol) of melamine and 9.9 g (0.098 mol) of triethylamine were added to 125.0 g (0.098 mol) of polyisobutenylsuccinic anhydride having a hydrolysis number of 87.5 mg KOH/g ($M_{reactive}$=1282 g/mol) and heated to 90° C. The resulting reaction mixture was stirred for 6 hours at 90° C. and then cooled to room temperature. After distillation of the triethylamine, 115.6 g of mixture I.9 according to the invention were obtained as a homogeneous, dark brown, thick and tacky condensate. The dynamic viscosity was 56 500 mPa·s at 40° C.

Characteristic peaks in the IR Spectrum: 1780 cm$^{-1}$ and 1716 cm$^{-1}$.

I.10 Preparation of Mixture I.10 According to the Invention

In a stirred apparatus, 19.73 g (0.156 mol) of melamine were added to 125.0 g (0.469 mol) of dodecenylsuccinic anhydride and heated to 300° C. The resulting reaction mixture was stirred for 4 hours at 300° C. and then cooled to room temperature. 120.5 g of mixture I.10 according to the invention were obtained as a turbid, light brown, thick condensate. The dynamic viscosity was 74 100 mPa·s at 40° C. Characteristic peaks in the IR spectrum: 1778 cm$^{-1}$ and 1712 cm$^{-1}$.

II. Production of leather

II.1 Preparation of Fatliquoring Agents

In a stirred flask, 2.3 g of a polyisobutene (Ma: 1000 g/mol) were mixed with 300 g of n-$C_{18}H_{37}O(CH_2CH_2O)_{25}H$, 400 g of oleic acid and 2.3 kg of sulfited, oxidized triolein and heated to 60° C. 4.7 l of water and 100 g of n-$C_{18}H_{37}O$ $(CH_2CH_2O)_7H$ were then added. The emulsion formed was passed through a gap homogenizer and cooled to room temperature. Fatliquor FL-1 was obtained.

In each case 92% by weight of the fatliquoring agent FL-1 (see below) and in each case 8% by weight of the mixtures I.1 to I.6 according to the invention were mixed in each case in a beaker by means of a commercial bar mixer from IKA. Fatliquoring agents F.1 to F.6 according to table 1 were obtained.

TABLE 1

Composition of fatliquoring agents F.1 to F.6

| Fatliquoring agent | FL-1 [% by wt.] | (Mixture) [% by wt.] |
|---|---|---|
| F.1 | 92 | 8 (I.1) |
| F.2 | 92 | 8 (I.2) |
| F.3 | 92 | 8 (I.3) |
| F.4 | 92 | 8 (I.4) |
| F.5 | 92 | 8 (I.5) |
| F.6 | 92 | 8 (I.6) |

II.2 Retanning of Leather

Data in % by weight relate to the active substance and are based in each case on the shaved weight, unless stated otherwise.

100 parts by weight of chrome-tanned cattle leather having a shaved thickness of from 1.8 to 2.0 mm were drummed with 200% by weight of water in a rotatable barrel (50 l) having baffles at 30° C. for 10 minutes. Thereafter, the water was discharged and the cattle leather was drummed with 1% by weight of sodium formate and 1.5% by weight of a napthalenesulfonic acid/formaldehyde condensate, prepared according to U.S. Pat. No. 5,186,846, example "Dispersant 1", in 100% by weight of water (60 minutes), neutralization taking place. The cattle leather pretreated in this manner was then cut in the butt region into 7 strips of about 500 g each. The retanning was effected up to the differentiation step by addition of the respective mixture according to the invention in a barrel and was completed only thereafter in seven separate 10 l dose barrels.

The pH of the leathers and leather liquor was increased to 7 in four steps with in each case 1.5% by weight of $NaHCO_3$. Thereafter, 10% by weight of dye from WO 05/040490, example 17 g (black), were added and drumming was effected for 40 minutes at pH of 7. The pH was increased to 9.6 with 8% by weight of sodium carbonate and drumming was effected for a further 80 minutes. Thereafter, washing was effected twice with 300% by weight of water in each case and the wash water was discarded. In a fresh liquor composed of 150% by weight of water and 1.5% by weight of formic acid (pH 5.6), drumming was effected for 50 minutes. After the fresh liquor had been discharged, the leathers were distributed over the seven separate 10 l dose barrels and, for the purpose of retanning, first 80% by weight of water and 2% by weight of a water repellant according to WO 2004/072307, example 1, formulation 1.1, were metered in each case in succession. After 10 minutes, 6% by weight of sulfone tanning agent from EP-B 0 459 168, example K1, were added and drumming was effected for a further 30 minutes.

The fatliquoring was effected by addition of 14% by weight of fatliquoring agent according to tables 1 and 2. In the comparative experiment, treatment was effected with 14% of FI-1. After a drumming time of 60 minutes, a pH of 3.5 was established by metering altogether 5% by weight of formic acid in portions. The liquor was discharged and washing was then effected with 300% by weight of water. The leather thus obtainable was dried at 45° C. and 20 mbar over a period of 6 minutes. After the leathers had been staked and allowed to stand (4 h at 20° C.), the leathers L1 to L6 according to the invention and the comparative leather C-L7 (cf. table 2) were tested. Thereafter, the leathers L1 to L6 according to the invention and the comparative leather C-L7 were subjected to a three-stage machine wash cycle according to DIN EN ISO 15702 and then rated again (table 3).

TABLE 2

Performance characteristics of the leathers L1 to L6 according to the invention and comparative leather C-L7

| Example | Fatliquoring agent | Leather | Fullness | Softness | Dyeing: Levelness | Dyeing: Intensity, brilliance | Grain tightness | Exhaustion |
|---|---|---|---|---|---|---|---|---|
| I.1 | F.1 | L1 | 2.5 | 3 | 2.5 | 2.5 | 2 | 1.5 |
| I.2 | F.2 | L2 | 1.5 | 2 | 2 | 1.5 | 2 | 1.5 |
| I.3 | F.3 | L3 | 2 | 2.5 | 2 | 2 | 2.5 | 2 |
| I.4 | F.4 | L4 | 3 | 3 | 2.5 | 3 | 3 | 2 |
| I.5 | F.5 | L5 | 2.5 | 2 | 3 | 2.5 | 2.5 | 2 |
| I.6 | F.6 | L6 | 2 | 2.5 | 2.5 | 3 | 2 | 2 |
| C-I.7 | FL-1 | C-L7 | 3 | 3.5 | 2.5 | 3 | 2.5 | 3 |

Remarks:

The rating was effected according to a rating system from 1 (very good) to 5 (poor).

TABLE 3

Performance characteristics of the leathers L1 to L7 according to the invention after the three-stage wash cycle according to DIN EN ISO 15702

| Fatliquoring agent | Leather | Fullness | Softness | Dyeing: Levelness | Dyeing: Intensity, brilliance | Grain tightness | Exhaustion |
|---|---|---|---|---|---|---|---|
| F.1 | L1 | 2.5 | 3 | 2.5 | 2.5 | 2.5 | 1.5 |
| F.2 | L2 | 2 | 2 | 1.5 | 2 | 2 | 2 |
| F.3 | L3 | 2 | 2.5 | 2 | 2 | 2.5 | 2.5 |
| F.4 | L4 | 3 | 3 | 2.5 | 3 | 3 | 3 |
| F.5 | L5 | 3.5 | 2.5 | 3 | 3 | 3 | 2 |
| F.6 | L6 | 2.5 | 3 | 3 | 3 | 2.5 | 3 |
| FL-1 | C-L7 | 4 | 5 | 4 | 5 | 3.5 | 5 |

It is striking that the leathers according to the invention are per se softer and rounder than the comparative leather. Particularly with regard to the dyeing, the differences after the three-stage machine wash cycle are even more striking. The comparative leather C-L7 can no longer be designated as agreeable leather after passing through the three-stage machine wash cycle.

We claim:

1. A process for the production of leather using one or more reaction products of
   (a) melamine or higher amines, wherein the higher amines are condensation products of melamine with at least one carbonyl compound selected from formaldehyde, acetaldehyde and urea
   (b) with at least one compound of the formula I $$A^1\text{-}R^1 \qquad\qquad I$$

wherein $R^1$ is selected from hydrocarbon radicals having 10 to 5000 carbon atoms, straight-chain or branched, saturated or having from one to three C—C double bonds, and $A^1$ from groups capable of reacting with amines.

2. The process according to claim 1, wherein $R^1$ is a hydrocarbon radical of the formula

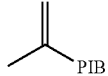

or a n-$C_{12}$-$C_{40}$-alkyl radical, PIB being a radical which is derived from polyisobutene.

3. The process according to claim 1, wherein $A^1$ is selected from acid chloride groups, $C_1$-$C_4$-alkyl ester groups and carboxylic anhydride groups.

4. The process according to claim 1, wherein treatment with at least one hydrophobic compound selected from hydrophobic silicones, polyisobutene and natural fats is additionally effected.

5. A leather produced using one or more reaction products of:
   (a) melamine or higher amines, wherein the higher amines are condensation products of melamine with at least one carbonyl compound selected from formaldehyde, acetaldehyde and urea
   (b) with at least one compound of the formula I $$A^1\text{-}R^1 \qquad\qquad I$$

wherein $R^1$ is selected from hydrocarbon radicals having 10 to 5000 carbon atoms, straight-chain or branched, saturated or having from one to three C—C double bonds, and $A^1$ from groups capable of reacting with amines.

6. An article of clothing produced using leather according to claim 5.

7. An interior automotive part produced using leather according to claim 5.

8. The process according to claim 1, which is carried out as a tanning process or as a retanning process.

* * * * *